United States Patent
Ryu et al.

(10) Patent No.: US 9,335,314 B2
(45) Date of Patent: May 10, 2016

(54) OPTICAL CIRCUIT-TYPE REFORMULATED FUEL DETECTING SENSOR DEVICE AND METHOD FOR MANUFACTURING SENSOR ELEMENT THEREOF

(71) Applicant: Electronics and Telecommunications Research Institute, Daejeon (KR)

(72) Inventors: Jin-Hwa Ryu, Ulsan (KR); Kyu-Ha Baek, Daejeon (KR); Lee-Mi Do, Daejeon (KR); Kang-Bok Lee, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 210 days.

(21) Appl. No.: 14/253,335

(22) Filed: Apr. 15, 2014

(65) Prior Publication Data

US 2015/0136959 A1    May 21, 2015

(30) Foreign Application Priority Data

Nov. 19, 2013  (KR) ......................... 10-2013-0140951

(51) Int. Cl.
*G01N 33/22*  (2006.01)
*G01N 21/3577*  (2014.01)
*G01N 21/552*  (2014.01)

(52) U.S. Cl.
CPC ............ *G01N 33/22* (2013.01); *G01N 21/3577* (2013.01); *G01N 21/552* (2013.01); *G01N 2201/08* (2013.01); *Y10T 29/4913* (2015.01)

(58) Field of Classification Search
CPC . G01N 33/22; G01N 21/17; G01N 2201/082; G01N 2201/08; G01N 2201/068; G01N 21/3577; G01N 21/552; Y10T 29/4913

USPC ............. 250/227.11, 573, 577; 356/432–436
See application file for complete search history.

(56) References Cited

U.S. PATENT DOCUMENTS

| | | | | |
|---|---|---|---|---|
| 5,200,064 A | * | 4/1993 | Russ ................. | G01N 33/2829 210/236 |
| 6,121,628 A | * | 9/2000 | Rising .................... | F23N 5/082 250/573 |
| 6,831,290 B2 | * | 12/2004 | Mentzer ................ | G01F 23/292 250/227.14 |
| 7,710,567 B1 | * | 5/2010 | Mentzer .............. | G01F 23/2924 250/577 |

FOREIGN PATENT DOCUMENTS

| KR | 1020050015933 A | 2/2005 |
|---|---|---|
| KR | 200445853 Y1 | 8/2009 |
| KR | 101170932 B1 | 7/2012 |

* cited by examiner

*Primary Examiner* — Seung C Sohn
(74) *Attorney, Agent, or Firm* — William Park & Associates Ltd.

(57) ABSTRACT

Disclosed herein is an optical circuit-type reformulated fuel detecting sensor device. The optical circuit-type reformulated fuel detecting sensor device includes: an optical source part generating optical signals having a single wavelength; a sensor part receiving the optical signals generated by the optical source part and outputting a reference optical signal and a sensed signal; a first photo-detector receiving the reference optical signal and outputting a reference optical output signal; a second photo-detector receiving the sensed signal and outputting a sensed optical output signal; an operation controlling part receiving the reference optical output signal and the sensed optical output signal and determining characteristics of fuel; and an output part receiving and outputting a result of the operation controlling part.

18 Claims, 5 Drawing Sheets

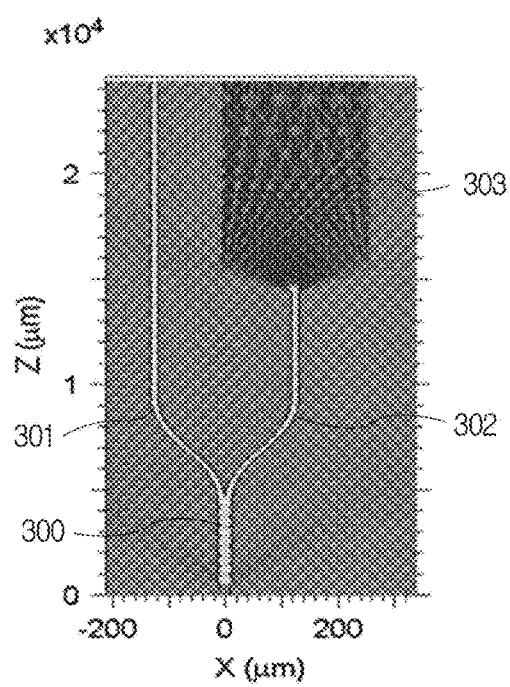

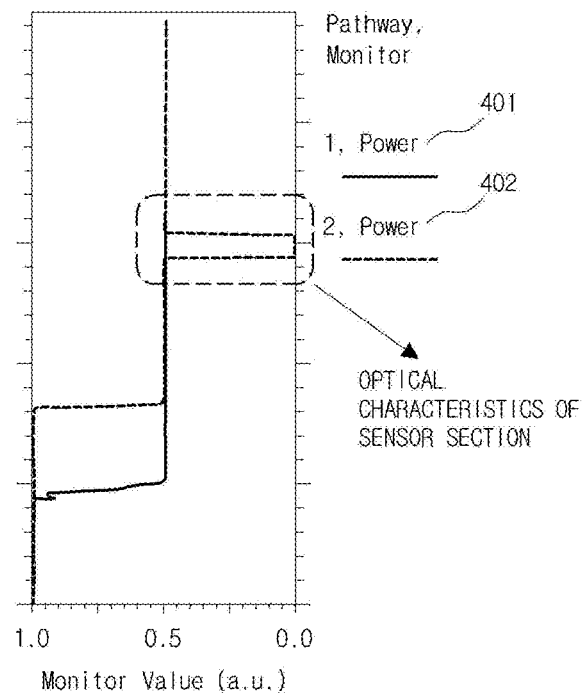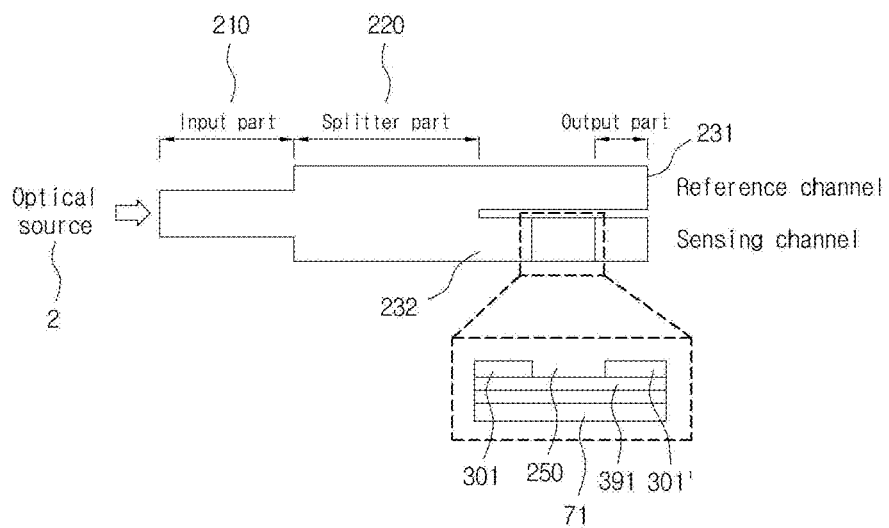

FIG. 7
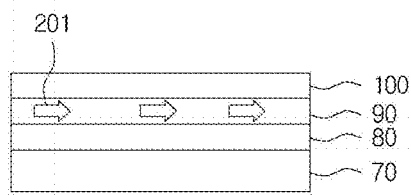
(a)
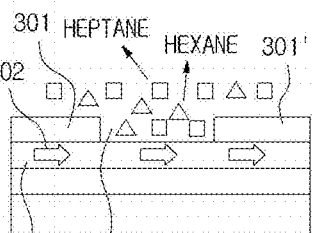
(b)
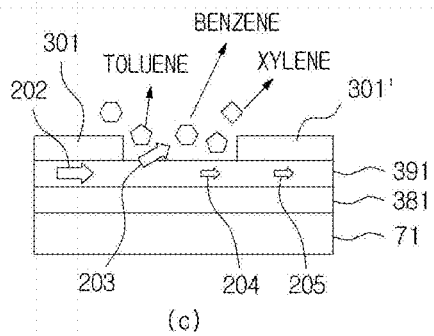
(c)

OPTICAL CIRCUIT-TYPE REFORMULATED FUEL DETECTING SENSOR DEVICE AND METHOD FOR MANUFACTURING SENSOR ELEMENT THEREOF

CROSS REFERENCE TO RELATED APPLICATION

This application claims the benefit of Korean Patent Application No. 10-2013-0140951, entitled "Optical Circuit-Type Reformulated Fuel Detecting Sensor Device and Method for Manufacturing Sensor Element Thereof", which is hereby incorporated by reference in its entirety into this application.

BACKGROUND OF THE INVENTION

1. Technical Field

The present invention relates to an optical circuit-type reformulated fuel detecting sensor, and more particularly, to an optical circuit-type reformulated fuel detecting sensor device and a method for manufacturing a sensor element thereof capable of determining reformulated gasoline used as fuel of a vehicle using optical characteristics of an optical signal.

2. Description of the Related Art

Recently, reformulated fuel (reformulated gasoline) has been deceived and sold as normal fuel in the market, which has been emerged as a serious social problem. In 2013, Korean petroleum quality and distribution authority has revealed that the amount of the tax evasion of the reformulated fuel is estimated to be one trillion won or more. The reformulated gasoline indicates a product produced similarly to gasoline so as to be sold as gasoline for a vehicle in order to gain an undue profit corresponding to a cost difference between the reformulated gasoline and fuel for a vehicle (normal fuel). Under the current Petroleum Business Law, in fuel of a vehicle depending on a rule of Section 1 of Article 2 of the Automobile Management Law and a machine and a vehicle depending on rules of each section of Article 2 of Enforcement Decree of the same law (using gasoline as fuel), a product produced by a method of mixing another petroleum product or petrochemicals with gasoline for a vehicle (including mixing between different kinds or grades of petroleum products), a method of mixing another petrochemicals with petrochemicals, or the like, has been defined as the reformulated gasoline. (Article 26 of the Petroleum Business Law and Article 30 of Enforcement Decree of the same law)

Reformulated gasoline that has been recently distributed has been produced by mixing an aromatic compound including toluene and an alcohol based petrochemical product such as methanol to a solvent (industrial gasoline) in an appropriate ratio, and the reformulated gasoline mixed with normal gasoline in a predetermined ratio has been distributed.

As a method for detecting reformulated fuel, a method for detecting reformulated fuel based on an ingredient analysis using a device such as a gas chromatography-mass spectroscopy (GC/MS) or a Fourier transform infrared spectroscopy (FT-IR) is used.

However, the method for detecting reformulated fuel based on an ingredient analysis has a limitation in performing search in real time in view of effectiveness such as a device using cost, a time, accessibility, and the like.

In addition, a method for measuring waveform deduction of a specific material among chemical materials using a principle such as infrared spectroscopy according to the related art has been developed, and research into a method for determining reformulated fuel using one or more colored dyes of which a color is changed in response to a gasoline component has been continuously conducted.

As the related art for this, Korean Patent Publication No. 10-1170932 (Adulterated Gasoline Detecting Method Using Polymer Sensor Fibers Including Polydiacetylene, and Device Including the Polymer Sensor Fibers) has disclosed a technology of easily determining reformulated gasoline with the naked eyes using polymer fibers selectively reacting to toluene, which is a specific component added for manufacturing the reformulated gasoline.

In addition, Korean Utility Model Publication No. 20-0445853 (Detector of Fuel Oil) has disclosed a technology of determining reformulated fuel by a portable reformulated fuel detecting device including an infrared light source, a cell holder, a detecting part, an operating part, and a display part by using optical characteristics (intrinsic absorption ratio of a specific waveform) of components such as toluene, thinner, bio-diesel, and the like, added to the reformulated fuel.

In the recent technology of determining reformulated fuel as described above, a method of picking target fuel to be measured and detecting an aromatic compound such as toluene, or the like, included in the reformulated fuel has been conducted.

Gasoline is a mixture of hydrocarbons having about 6 to 10 carbons. In molecular structures of materials configuring crude oil, the number of hydrocarbons having a straight chain shape is many, such that a problem such as knocking or easy ignition occurs. Therefore, oil refining companies add cyclic benzene or toluene to crude oil to somewhat increase an octane number, thereby allowing the crude oil to which the cyclic benzene or toluene is added to be used in a vehicle engine.

Therefore, even though content component ratios are different from each other per oil refining company, the aromatic compound such as toluene, or the like, is present even in valid gasoline. Therefore, there is a limitation in accurately determining whether or not gasoline is the reformulated gasoline only with qualitative determination depending on whether or not a toluene component is present.

In addition, in a scheme of collecting reformulated fuel samples that frequently appear and studying the reformulated fuel samples in a laboratory, it is difficult to perform a real-time analysis, a large cost is required, and a device has a large volume, such that it is difficult to install the device in the field and perform real-time determination.

Therefore, a reformulated fuel detecting device that is capable of quantitatively contrasting characteristics of the reformulated gasoline with each other in real time, is simply carried, and is cheap has been demanded.

The present invention relates to an optical circuit-type reformulated fuel detecting sensor device and method using an optical circuit. The background technology for an optical branching component has been disclosed in Korean Patent Laid-Open Publication No. 2005-0015933.

RELATED ART DOCUMENT

Patent Document (Patent Document 1) Korean Patent Publication No. 10-1170932 (Adulterated Gasoline Detecting Method Using Polymer Sensor Fibers Including Polydiacetylene, and Device Including the Polymer Sensor Fibers)

(Patent Document 2) Korean Utility Model Publication No. 20-0445853 (Detector of Fuel Oil)

(Patent Document 3) Korean Patent Laid-Open Publication No. 2005-0015933 (Optical Branching Waveguide)

SUMMARY OF THE INVENTION

An object of the present invention is to provide an optical circuit-type reformulated fuel detecting sensor device and a method for manufacturing a sensor element thereof capable of determining reformulated gasoline in real time by quantitatively measuring test fuel using optical characteristics of toluene added for manufacturing the reformulated fuel.

Another object of the present invention is to provide an optical circuit-type reformulated fuel detecting sensor device and a method for manufacturing a sensor element thereof in which a sensor for determining reformulated fuel containing a reformulated component may be manufactured in a plane optical circuit-type high integrated structure.

According to an exemplary embodiment of the present invention, there is provided an optical circuit-type reformulated fuel detecting sensor device including: an optical source part generating optical signals having a single wavelength; a sensor part receiving the optical signals generated by the optical source part and outputting a reference optical signal and a sensed signal for test fuel; a first photo-detector receiving the reference optical signal and outputting a reference optical output signal; a second photo-detector receiving the sensed signal and outputting a sensed optical output signal; an operation controlling part receiving the reference optical output signal and the sensed optical output signal and determining characteristics of the fuel; and an output part receiving and outputting a result of the operation controlling part.

The sensor part may include: an optical input part receiving the optical signals generated by the optical source part; an optical signal splitter part uniformly splitting the optical signals incident from the optical input part into first and second optical signals; a reference channel part receiving the first optical signal and outputting the reference optical signal; and a sensing channel part receiving the second optical signal and passing the test fuel therethrough to output the sensed optical signal, and the sensor part may be formed of a plane optical circuit-type sensor element.

The reference channel part may include: a first core layer through which the first optical signal passes; a first upper clad layer formed on the first core layer; and a first under clad layer formed beneath the first core layer, wherein the first core layer has a refractive index higher than those of the first upper clad layer and the first under clad layer and has a refractive index between a refractive index of additive oil added for manufacturing reformulated fuel and a refractive index of a normal fuel component.

The sensing channel part may include: a second core layer through which the second optical signal passes; a second upper clad layer formed on the second core layer; a second under clad layer formed beneath the second core layer; and a sample part formed in central sections of the second upper clad layer and the second core layer and formed of a space part cut in a groove part shape up to an upper surface of the second under clad layer, wherein the second core layer has a refractive index higher than those of the second upper clad layer and the second under clad layer and has a refractive index between the refractive index of the additive oil added for manufacturing the reformulated fuel and the refractive index of the normal fuel component.

The sensing channel part may include: a second core layer through which the second optical signal passes; a second upper clad layer formed on the second core layer; a second under clad layer formed beneath the second core layer; and a sample part formed in a central section of the second upper clad layer and formed of a space part cut in a groove part shape up to an upper surface of the second core layer, wherein the second core layer has a refractive index higher than those of the second upper clad layer and the second under clad layer and has a refractive index between the refractive index of the additive oil added for manufacturing the reformulated fuel and the refractive index of the normal fuel component.

The first and second photo-detectors may detect and output powers of the optical outputs or light transmittances.

The optical source part may generate optical signals having a wavelength of 2.17 μm.

The refractive index of the first core layer or the second core layer may be 1.42 to 1.48.

The operation controlling part may compare the reference optical output signal and the sensed optical output signal with each other to determine whether or not the test fuel is reformulated fuel.

According to another exemplary embodiment of the present invention, there is provided a method for manufacturing an optical circuit-type reformulated fuel detecting sensor element, including: forming a substrate; forming an optical input part and an optical signal splitter part on the substrate; and forming a reference channel part and a sensing channel part each split from the optical signal splitter part, wherein the sensing channel part includes: a second under clad layer formed on the substrate; a second core layer formed on the second under clad layer; a second upper clad layer formed on the second core layer; and a sample part formed in central sections of the second upper clad layer and the second core layer and formed of a space part cut in a groove part shape up to an upper surface of the second under clad layer.

According to still another exemplary embodiment of the present invention, there is provided a method for manufacturing an optical circuit-type reformulated fuel detecting sensor element, including: forming a substrate; forming an optical input part and an optical signal splitter part on the substrate; and forming a reference channel part and a sensing channel part each split from the optical signal splitter part, wherein the sensing channel part includes: a second under clad layer formed on the substrate; a second core layer formed on the second under clad layer; a second upper clad layer formed on the second core layer; and a sample part formed in a central section of the second upper clad layer and formed of a space part cut in a groove part shape up to an upper surface of the second core layer.

The reference channel part may include: a first under clad layer formed on the substrate; a first core layer formed on the first under clad layer; and a first upper clad layer formed on the first core layer, and the first and second core layers may be made of a material having refractive indices higher than those of the first and second upper clad layers and the first and second under clad layers and having refractive indices between a refractive index of additive oil added for manufacturing reformulated fuel and a refractive index of a normal fuel component.

BRIEF DESCRIPTION OF THE DRAWINGS

FIG. 4 shows a simulation result for a trajectory of an optical signal in the optical circuit-type reformulated fuel detecting sensor device according to an exemplary embodiment of the present invention;

FIG. 5 is a graph showing a power of an optical output for the simulation result of FIG. 4;

FIG. 6 shows a structure of an optical circuit-type reformulated fuel detecting sensor element according to another exemplary embodiment of the present invention; and FIGS. 7(a) to 7(c) show a process in which optical signals pass through a reference channel part and a sensing channel part according to another exemplary embodiment of the present invention.

DESCRIPTION OF EXEMPLARY EMBODIMENTS

The present invention may be variously modified and have several forms. Therefore, specific exemplary embodiments of the present invention will be illustrated in the accompanying drawings and be described in detail in the present specification. However, it is to be understood that the present invention is not limited to a specific exemplary embodiment, but includes all modifications, equivalents, and substitutions without departing from the scope and spirit of the present invention. When it is determined that the detailed description of the known art related to the present invention may obscure the gist of the present invention, the detailed description thereof will be omitted.

Terms used in the specification, 'first', 'second', etc., may be used to describe various components, but the components are not to be interpreted to be limited to the terms. The terms are used to distinguish one component from another component.

Terms used in the present specification are used only in order to describe specific exemplary embodiments rather than limiting the present invention. Singular forms are intended to include plural forms unless the context clearly indicates otherwise. It will be further understood that the terms "comprises" or "have" used in this specification, specify the presence of stated features, steps, operations, components, parts mentioned in this specification, or a combination thereof, but do not preclude the presence or addition of one or more other features, numerals, steps, operations, components, parts, or a combination thereof.

Hereinafter, exemplary embodiments of the present invention will be described in detail with reference to the accompanying drawings.

Figure 1:
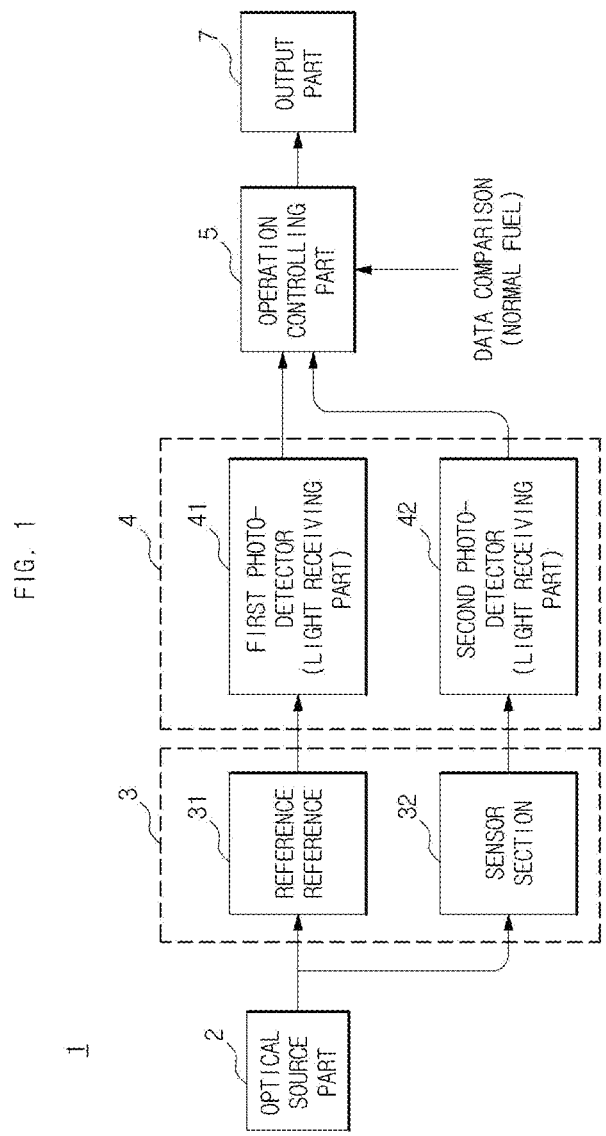
FIG. 1 is a block diagram of an optical circuit-type reformulated fuel detecting sensor device according to an exemplary embodiment of the present invention.

FIG. 1 is a block diagram of an optical circuit-type reformulated fuel detecting sensor device according to an exemplary embodiment of the present invention.

The optical circuit-type reformulated fuel detecting sensor device 1 according to an exemplary embodiment of the present invention is configured to include an optical source part 2, a sensor part 3, a detecting part 4, an operation controlling part 5, and an output part 7.

According to an exemplary embodiment of the present invention, the sensor part 3 includes a reference channel part 31 receiving optical signals generated by the optical source part 2 and outputting a reference optical signal and a sensing channel part 32 outputting a sensed signal.

The sensor part 3 may be manufactured as a single chip of an optical circuit-type reformulated fuel detecting sensor element.

In the following detailed description of the present invention, the sensor part 3 means an optical circuit-type reformulated fuel detecting sensor element.

The optical signal generated by the optical source part 2 is split into two optical signals by the sensor part 3, wherein one of the two optical signals passes through a section of the reference channel part 31 of the sensor part 3 and then progresses to a first photo-detector 41.

The other of the two signals passes through a section of the sensing channel part 32 of the sensor part 3 and then progresses to a second photo-detector 42. The used optical signal has absorption characteristics selectively high with respect to a specific component.

According to an exemplary embodiment of the present invention, a light source of the light source part 2 uses the same waveform as an absorption waveform of toluene added for manufacturing reformulated fuel. The toluene has optical characteristics that an absorption ratio thereof is increased at a waveform of 2.17 μm. Therefore, characteristics of the optical signal passing through the sensing channel part are changed by a concentration of specific component included in a reformulated fuel component. The two photo-detector signals progress to the operation controlling part 5. The operation controlling part 5 receives the two photo-detector signals and compares a light transmittance or a power of an optical output of sample fuel with a reference output signal to determine characteristics of the sample fuel.

The operation controlling part 5 compares data on the sample fuel with data on a pre-stored transmittance and output power of normal fuel and controls a display part (not shown) to display a characteristic result of the sample fuel through the output part 7.

The characteristic result of the fuel may be determined by comparing a degree of difference from the reference output signal with the stored data.

In addition, the output part 7 may transmit an output signal for the detection result to an external terminal.

Figure 2:
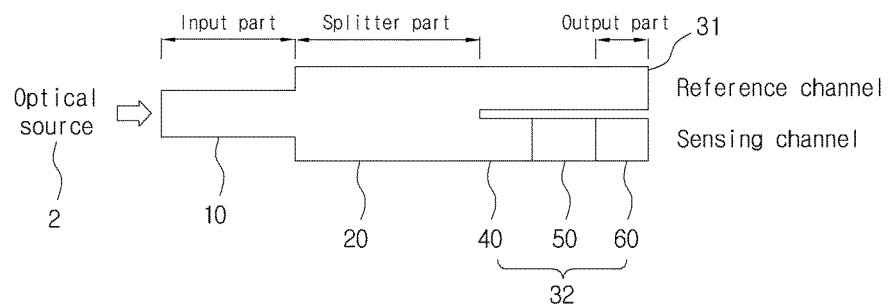
FIG. 2 shows a structure of an optical circuit-type reformulated fuel detecting sensor element according to an exemplary embodiment of the present invention.

FIG. 2 shows a structure of an optical circuit-type reformulated fuel detecting sensor element of the optical circuit-type reformulated fuel detecting sensor device according to an exemplary embodiment of the present invention.

The sensor part 3 according to an exemplary embodiment of the present invention may be manufactured as a single chip of a plane optical circuit-type reformulated fuel detecting sensor element.

The optical circuit-type reformulated fuel detecting sensor element includes an optical input part 10 formed at the front, an optical signal splitter part 20 formed at a rear end of the optical input part, and a reference channel part 31 and a sensing channel part 32 that are formed at a rear end of the optical signal splitter part 20 and are split.

A base of the plane optical circuit-type reformulated fuel detecting sensor element according to an exemplary embodiment of the present invention may be manufactured on a specific substrate, wherein the substrate may be made of any one of substrate materials containing glass, quartz, silicon, resin, and the like.

The optical circuit-type reformulated fuel detecting sensor element according to an exemplary embodiment of the present invention may be manufactured by forming the optical input part and the optical signal splitter part on the substrate and then forming the reference channel part 31 and the sensing channel part 32.

Referring to FIG. 2, optical signals incident to the optical source part 2 are incident to the optical input part 10 of the sensor part.

The optical signals incident to the optical input part 10 are uniformly split into first and second optical signals by the optical signal splitter part 20 of an optical distribution element having uniform polarization characteristics.

The first and second optical signals progress to the reference channel part 31 and the sensing channel part 32, respectively.

The first optical signals of the split optical signals progress the reference channel part 31, and powers of optical outputs thereof are measured by the first photo-detector 41.

Referring to FIGS. 1 and 2, the outputs of the first optical signals measured by the first photo-detector 41 are input to the operation controlling part 5, and powers of the outputs of the first optical signal are provided as a reference signal to be compared with a sensed data by the operation controlling part 5.

In addition, the second optical signals progress to the sensing channel part 32. The second optical signals progressing to the sensing channel part 32 pass through a second optical signal input end 40 and then pass through a discontinuous channel section, that is, a sample part 50 in which the optical signals are exposed to the reformulated fuel component. After the second optical signals passing through the sample part 50 pass through a second optical signal output end 60, powers of the optical outputs of the second optical signals or light transmittances of the second optical signals are measured by the second photo-detector 42.

In order to measure the power of the optical output, a semiconductor optical output measuring device using a photodiode light receiving element may be used as the first and second optical photo-detectors.

In another exemplary embodiment of the present invention, the first and second photo-detectors measures a light transmittance, and the operation controlling part 5 compares the first and second output signals with each other, thereby making it possible to determine whether or not the fuel is the reformulated fuel.

In this case, in order to measure the light transmittance, a spectrophotometer measuring a transmittance for monochromatic light may be used as the first and second photo-detectors.

The optical source according to an exemplary embodiment of the present invention uses the same waveform as an absorption waveform of toluene added for manufacturing the reformulated fuel. The toluene has optical characteristics that an absorption ratio thereof is increased at a waveform of 2.17 μm.

According to an exemplary embodiment of the present invention, the second optical signal output end 60 behind the sample part 50 in the sensing channel part 32 is formed so as to be larger than the input end 40 of the sensing channel part 32 in consideration of a dispersion angle and scattering characteristics of the sample part 50.

According to an exemplary embodiment of the present invention, since the first optical signal passing through the reference channel part 31 is provided as a reference signal data compared with the power of the optical output of the second optical signal by the operation controlling part 5, an error of an optical signal operation control due to aging of the optical source and a change in the optical output may be prevented.

According to another exemplary embodiment of the present invention, in a range in which an output of the optical source is constant, the reference channel part may be omitted. That is, the operation controlling part 5 may determine the reference signal compared with the sensed data by receiving a reference optical signal output from a database instead of the reference channel part.

The optical signal used in an exemplary embodiment of the present invention has absorption characteristics selectively high with respect to toluene, benzene, xylene, and a specific component. Therefore, characteristics of the optical signals passing through the sensor section are changed by a concentration of specific component included in a reformulated fuel component.

The operation controlling part 5 compares the light transmittance or the power of the optical output of the measured fuel (sample) with the reference output signal to determine whether or not the measured fuel is the reformulated fuel.

Figure 3:
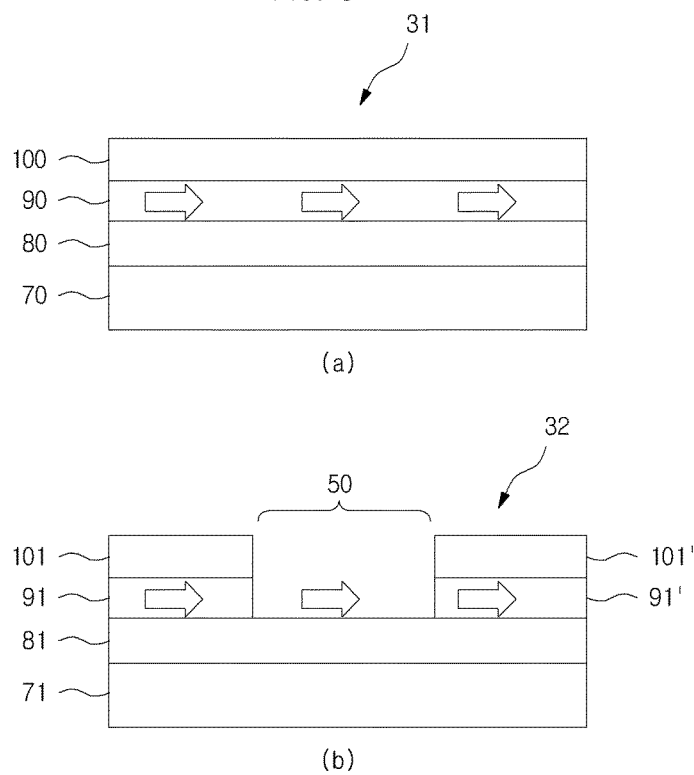
FIGS. 3(a) and 3(b) show structures of a reference channel part and a sensing channel part of a sensor part according to an exemplary embodiment of the present invention, respectively.

FIGS. 3(*a*) and 3(*b*) show structures of a reference channel part and a sensing channel part of a sensor part according to an exemplary embodiment of the present invention, respectively.

FIG. 3(*a*) shows a structure of the reference channel part 31 of the sensor part 3 according to an exemplary embodiment of the present invention.

Referring to FIGS. 3(*a*) and 3(*b*), the optical circuit-type reformulated fuel detecting sensor element may be manufactured in a flat shape.

A base of the optical circuit-type reformulated fuel detecting sensor element according to an exemplary embodiment of the present invention may be manufactured on a specific substrate, wherein the substrate may be made of any one of substrate materials containing glass, quartz, silicon, resin, and the like.

Referring to FIG. 3(*a*), the reference channel part 31 includes a substrate layer 70, a under clad layer 80 formed on the substrate layer 70, a core layer 90 formed on the under clad layer 80, and an upper clad layer 100 formed on the core layer 90.

FIG. 3B shows a structure of the sensing channel part of the sensor part according to an exemplary embodiment of the present invention.

Referring to FIG. 3(*b*), the sensing channel part 32 includes a substrate layer 71, a under clad layer 81 formed on the substrate layer 71, a core layer 91 formed on the under clad layer 81, and an upper clad layer 101 formed on the core layer 91, wherein the upper clad layer 101 and the core layer 91 have a sample part 50 formed in partial sections of the centers thereof and formed of a space part cut in a groove part shape up to an upper surface of the under clad layer.

The sample part 50 formed of the space part accommodates a reformulated fuel sample to be measured.

The core layer 90 or 91 serves as a waveguide guiding the first or second optical signals split by the optical signal splitter part 20 so as to progress to the first or second photo-detector.

According to an exemplary embodiment of the present invention, the core layer 90 or 91 has a refractive index between a refractive index of a component added for manufacturing the reformulated fuel and a refractive index of normal fuel.

Normal gasoline in which various hydrocarbons having about 5 to 10 carbons are mixed with each other has a structure of alkane or alkene. These materials generally have a refractive index of 1.33 to 1.41. However, the toluene added to the reformulated fuel, the benzene, and the xylene have a refractive index of 1.49 to 1.51. As a specific example, heptane and hexane configuring the gasoline have refractive indices of 1.3876 and 1.3749, respectively, and the toluene has a refractive index of 1.4969.

According to an exemplary embodiment of the present invention, the core layer 90 or 91 has a refractive index of 1.42 to 1.48, which is a range between the refractive index of the component added for manufacturing the reformulated fuel and the refractive index of the normal fuel.

The upper and under clad layers 100 or 101 and 80 or 81 are positioned on and beneath of the core layer 90 or 91 and serve to induce the first and second optical signals to progress within the core layer.

According to an exemplary embodiment of the present invention, the core layer 90 or 91 has a refractive index higher than those of the upper and under clad layers 100 or 101 and 80 or 81 in order to prevent the first and second optical signals from being leaked to the clad layers outside the core layer 90 or 91.

Referring to FIG. 3A, the first optical signals split by the optical signal splitter part 20 pass through the core layer 90 of the reference channel part 31 and then progress directly to the first photo-detector 41.

Referring to FIGS. 2 and 3B, the second optical signals split by the optical signal splitter part 20 pass through an input end core layer 91 of the sensing channel part 32, pass through the sample part 50 exposed to the reformulated fuel component, pass through an output end core layer 91', and then progress to the second photo-detector 42.

That is, the second optical signals pass through a structure of discontinuous core layers 91 and 91'.

FIG. 4 shows a simulation result for a trajectory of an optical signal in the optical circuit-type reformulated fuel detecting sensor device according to an exemplary embodiment of the present invention.

A simulation according to an exemplary embodiment of the present invention was performed based on a 1×2 plane optical distribution element distributing one optical signal in a ratio of 50:50 in a state in which a waveform of an optical source is to 2.17 μm, which is an intrinsic absorption waveform of a toluene component.

The simulation was performed using normal fuel as a sample in a structure for minimizing a loss of an optical signal scattered by discontinuous core layers 91 and 91'.

Referring to FIG. 4, first optical signals 301 split from an incident optical signals 300 pass through the core layer 90 of the reference channel part and then progress directly to the first photo-detector 41.

In addition, optical signals scattered by the discontinuous core layer are received by the core layer 91' while second optical signals 302 split from the incident optical signals 300 pass through the sample part 50 of the sensing channel part 32, and resultant optical signals pass through the core layer 91' and then progress the second photo-detector 42. The simulation shows a result that the optical signals scattered by the discontinuous core layer of the sensing channel part 32, that is, the sample part 50 are maximally received, such that a loss of the optical signals received by the second photo-detector 42 is minimized as compared with the optical signals received by the first photo-detector 41.

FIG. 5 is a graph showing a power of an optical output for the simulation result of FIG. 4.

Referring to FIG. 5, a power of an output of the first optical signal detected by the first photo-detector 41 is represented by Power 1 401, and a power of an output of the second optical signal detected by the second photo-detector 42 is represented by Power 2 402.

In FIG. 5, it was measured that a ratio between the powers of the optical outputs received by the first and second photo-detectors 41 and 42 is 49.4%:49.2% based on an input optical signal. It may be appreciated from the simulation result that when the normal fuel contacts the sample part 50, the optical output received by the second photo-detector 42 has a loss of 0.2% as compared with the optical output received by the first photo-detector 41. However, when the reformulated fuel containing the toluene component contacts the sample part 50, the optical signals arriving at the second photo-detector 42 are decreased dependently on a concentration of the toluene.

FIG. 6 shows a structure of an optical circuit-type reformulated fuel detecting sensor element according to another exemplary embodiment of the present invention.

Referring to FIG. 6, a reference channel part 231 has the same structure as that of the reference channel part of FIG. 2.

In addition, according to another exemplary embodiment of the present invention, in a range in which an output of the optical source is constant, the reference channel part may be omitted. That is, the operation controlling part 5 may determine the reference signal compared with the sensed data by receiving a reference optical signal output from a database instead of the reference channel part.

The optical circuit-type reformulated fuel detecting sensor element of FIG. 6 has the same structure as that of the optical circuit-type reformulated fuel detecting sensor element of FIG. 2 described above except for structures of a sensing channel part and a sample part 250.

Referring to FIG. 6, a core layer 391 of the sensing channel part has a continuous structure from an input end to an output end, and the sample part 250 is formed in partial sections of the centers of the upper clad layer 301 and is formed of a space part cut in a groove part shape up to an upper surface of the core layer 391.

When sample fuel is accommodated in the sample part 250, partial sections of the upper clad layers 301 and 301' are exposed to a fuel component.

The optical circuit-type reformulated fuel detecting sensor element according to an exemplary embodiment of the present invention has characteristics that the optical signals progress to only the core layer 391 due to a difference between refractive indices of the core layer 391 and the upper and under clad layers.

However, when the fuel is filled in the sample part 250, which is the space part formed at the center of the upper clad layers 301 and 301', some of the second optical signals are absorbed and dispersed by the sample part 250 due to a difference between a refractive index of the core layer 391 and a refractive index of the fuel component.

FIGS. 7(a) to 7(c) show a process in which optical signals pass through a reference channel part and a sensing channel part according to another exemplary embodiment of the present invention.

A reference channel part of FIG. 7(a) has the same structure as that of FIG. 3(a). Referring to FIGS. 6 and 7(a), first optical signals 201 split by an optical signal splitter part 220 pass through a core layer of the reference channel part and then progress directly to the first photo-detector 41.

FIG. 7(b) shows a process in which second optical signals pass through a sensing channel part according to another exemplary embodiment of the present invention in which normal fuel is accommodated.

Referring to FIG. 7(b), normal gasoline is accommodated in a sampling part 250 of the sensing channel part.

In addition, a core layer according to an exemplary embodiment of the present invention is manufactured so as to have a refractive index that is in the range of 1.42 to 1.48.

Normal gasoline in which various hydrocarbons having about 5 to 10 carbons are mixed with each other has a structure of alkane or alkene. These materials generally have a refractive index of 1.33 to 1.41.

Referring to FIG. 7(b), when the normal gasoline having the refractive index of 1.33 to 1.41 is accommodated in the sample part and the second optical signals pass through the core layer of the sensing channel part 232, an upper surface of the core layer 391 has a refractive index lower than that of the core layer 391, such that all of the second optical signals progress to the second photo-detector 42 along the core layer 391.

FIG. 7(c) shows a process in which second optical signals pass through a sensing channel part according to another exemplary embodiment of the present invention in which reformulated fuel is accommodated.

The toluene added to the reformulated fuel, the benzene, and the xylene have a refractive index of 1.49 to 1.51.

Referring to FIG. 79c), when the second optical signals passing through the core layer 391 are exposed to a reformulated fuel component such as the toluene, or the like, on an upper surface of the core part 391 in the sample part 250 section, some 203 of the optical signals are dispersed by the sample part 250 depending on a concentration of the toluene, or the like, based on waveguide characteristics of an optical circuit, and other optical signals 205 arrive at the second photo-detector 42.

Powers of outputs of the optical signals arriving at the second photo-detector 42 and powers of outputs of the optical signals arriving at the first photo-detector 41 are compared with each other by the operation controlling part 5, such that it is determined whether the fuel is the reformulated fuel depending on a difference between these powers.

With the optical circuit-type reformulated fuel detecting sensor device and the method for manufacturing a sensor element thereof according to an exemplary embodiment of the present invention, an optical reformulated fuel determining device may be embedded and manufactured as a high-integrated small chip, and the sensor may be manufactured by a basic lithography process technology, such that a microsensor may be manufactured at a low cost.

In addition, the optical circuit-type reformulated fuel detecting sensor device may have a high portability due to high integration, be installed in a narrow space, and perform quantitative measurement.

According to an exemplary embodiment of the present invention, since the first optical signal passing through the reference channel part is provided as a reference signal data compared with the power of the optical output of the second optical signal by the operation controlling part, an error of an optical signal operation control due to aging of the optical source and a change in the optical output may be prevented.

Hereinabove, although the optical circuit-type reformulated fuel detecting sensor device according to an exemplary embodiment of the present invention has a plane structure has been described, it may have structures having several forms, if necessary, in the case in which a curved waveguide is used.

The spirit of the present invention has been just exemplified. It will be appreciated by those skilled in the art that various modifications and alterations can be made without departing from the essential characteristics of the present invention.

Accordingly, the embodiments disclosed in the present invention and the accompanying drawings are used not to limit but to describe the spirit of the present invention. The scope of the present invention is not limited only to the embodiments and the accompanying drawings.

The scope of the present invention should be interpreted by the following claims and it should be interpreted that all spirits equivalent to the following claims fall within the scope of the present invention.

What is claimed is:

1. An optical circuit-type reformulated fuel detecting sensor device comprising:
   an optical source part generating optical signals having a single wavelength;
   a sensor part receiving the optical signals generated by the optical source part and outputting a reference optical signal and a sensed signal for test fuel;
   a first photo-detector receiving the reference optical signal and outputting a reference optical output signal;
   a second photo-detector receiving the sensed signal and outputting a sensed optical output signal;
   an operation controlling part receiving the reference optical output signal and the sensed optical output signal and determining characteristics of the fuel; and
   an output part receiving and outputting a result of the operation controlling part.

2. The optical circuit-type reformulated fuel detecting sensor device of claim 1, wherein the sensor part includes:
   an optical input part receiving the optical signals generated by the optical source part;
   an optical signal splitter part uniformly splitting the optical signals incident from the optical input part into first and second optical signals;
   a reference channel part receiving the first optical signal and outputting the reference optical signal; and
   a sensing channel part receiving the second optical signal and passing the test fuel therethrough to output the sensed optical signal, and
   the sensor part is formed of a plane optical circuit-type sensor element.

3. The optical circuit-type reformulated fuel detecting sensor device of claim 2, wherein the reference channel part includes:
   a first core layer through which the first optical signal passes;
   a first upper clad layer formed on the first core layer; and
   a first under clad layer formed beneath the first core layer,
   the first core layer having a refractive index higher than those of the first upper clad layer and the first under clad layer and having a refractive index between a refractive index of additive oil added for manufacturing reformulated fuel and a refractive index of a normal fuel component.

4. The optical circuit-type reformulated fuel detecting sensor device of claim 2, wherein the sensing channel part includes:
   a second core layer through which the second optical signal passes;
   a second upper clad layer formed on the second core layer;
   a second under clad layer formed beneath the second core layer; and
   a sample part formed in central sections of the second upper clad layer and the second core layer and formed of a space part cut in a groove part shape up to an upper surface of the second under clad layer,
   the second core layer having a refractive index higher than those of the second upper clad layer and the second under clad layer and having a refractive index between the refractive index of the additive oil added for manufacturing the reformulated fuel and the refractive index of the normal fuel component.

5. The optical circuit-type reformulated fuel detecting sensor device of claim 3, wherein the sensing channel part includes:
   a second core layer through which the second optical signal passes;
   a second upper clad layer formed on the second core layer;
   a second under clad layer formed beneath the second core layer; and
   a sample part formed in central sections of the second upper clad layer and the second core layer and formed of a space part cut in a groove part shape up to an upper surface of the second under clad layer, the second core layer having a refractive index higher than those of the second upper clad layer and the second under clad layer and having a refractive index between the refractive index of the additive oil added for manufacturing the reformulated fuel and the refractive index of the normal fuel component.

6. The optical circuit-type reformulated fuel detecting sensor device of claim 2, wherein the sensing channel part includes:
a second core layer through which the second optical signal passes;
a second upper clad layer formed on the second core layer;
a second under clad layer formed beneath the second core layer; and
a sample part formed in a central section of the second upper clad layer and formed of a space part cut in a groove part shape up to an upper surface of the second core layer,
the second core layer having a refractive index higher than those of the second upper clad layer and the second under clad layer and having a refractive index between the refractive index of the additive oil added for manufacturing the reformulated fuel and the refractive index of the normal fuel component.

7. The optical circuit-type reformulated fuel detecting sensor device of claim 3, wherein the sensing channel part includes:
a second core layer through which the second optical signal passes;
a second upper clad layer formed on the second core layer;
a second under clad layer formed beneath the second core layer; and
a sample part formed in a central section of the second upper clad layer and formed of a space part cut in a groove part shape up to an upper surface of the second core layer,
the second core layer having a refractive index higher than those of the second upper clad layer and the second under clad layer and having a refractive index between the refractive index of the additive oil added for manufacturing the reformulated fuel and the refractive index of the normal fuel component.

8. The optical circuit-type reformulated fuel detecting sensor device of claim 1, wherein the first and second photodetectors detect and output powers of the optical outputs or light transmittances.

9. The optical circuit-type reformulated fuel detecting sensor device of claim 1, wherein the optical source part generates optical signals having a wavelength of 2.17 µm.

10. The optical circuit-type reformulated fuel detecting sensor device of claim 3, wherein the refractive index of the first core layer is 1.42 to 1.48.

11. The optical circuit-type reformulated fuel detecting sensor device of claim 4, wherein the refractive index of the first core layer or the second core layer is 1.42 to 1.48.

12. The optical circuit-type reformulated fuel detecting sensor device of claim 6, wherein the refractive index of the first core layer or the second core layer is 1.42 to 1.48.

13. The optical circuit-type reformulated fuel detecting sensor device of claim 1, wherein the operation controlling part compares the reference optical output signal and the sensed optical output signal with each other to determine whether or not the test fuel is reformulated fuel.

14. A method for manufacturing an optical circuit-type reformulated fuel detecting sensor element, comprising:
forming a substrate;
forming an optical input part and an optical signal splitter part on the substrate; and
forming a reference channel part and a sensing channel part each split from the optical signal splitter part,
wherein the sensing channel part includes:
a second under clad layer formed on the substrate;
a second core layer formed on the second under clad layer;
a second upper clad layer formed on the second core layer; and
a sample part formed in central sections of the second upper clad layer and the second core layer and formed of a space part cut in a groove part shape up to an upper surface of the second under clad layer.

15. A method for manufacturing an optical circuit-type reformulated fuel detecting sensor element, comprising:
forming a substrate;
forming an optical input part and an optical signal splitter part on the substrate; and
forming a reference channel part and a sensing channel part each split from the optical signal splitter part,
wherein the sensing channel part includes:
a second under clad layer formed on the substrate;
a second core layer formed on the second under clad layer;
a second upper clad layer formed on the second core layer; and
a sample part formed in a central section of the second upper clad layer and formed of a space part cut in a groove part shape up to an upper surface of the second core layer.

16. The method for manufacturing an optical circuit-type reformulated fuel detecting sensor element of claim 14, wherein the reference channel part includes:
a first under clad layer formed on the substrate;
a first core layer formed on the first under clad layer; and
a first upper clad layer formed on the first core layer, and
the first and second core layers are made of a material having refractive indices higher than those of the first and second upper clad layers and the first and second under clad layers and having refractive indices between a refractive index of additive oil added for manufacturing reformulated fuel and a refractive index of a normal fuel component.

17. The method for manufacturing an optical circuit-type reformulated fuel detecting sensor element of claim 15, wherein the reference channel part includes:
a first under clad layer formed on the substrate;
a first core layer formed on the first under clad layer; and
a first upper clad layer formed on the first core layer, and
the first and second core layers are made of a material having refractive indices higher than those of the first and second upper clad layers and the first and second under clad layers and having refractive indices between a refractive index of additive oil added for manufacturing reformulated fuel and a refractive index of a normal fuel component.

18. The method for manufacturing an optical circuit-type reformulated fuel detecting sensor element of claim 16, wherein the refractive indices of the first and second core layers are 1.42 to 1.48.

* * * * *